(12) United States Patent
DiResta et al.

(10) Patent No.: US 6,547,777 B2
(45) Date of Patent: Apr. 15, 2003

(54) APPARATUS AND METHOD FOR REDUCING INTERSTITIAL FLUID PRESSURE AND ENHANCING DELIVERY OF A THERAPEUTIC AGENT

(75) Inventors: Gene R. DiResta, Pleasantville, NY (US); John Henry Healey, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/784,132

(22) Filed: Feb. 16, 2001

(65) Prior Publication Data

US 2001/0047152 A1 Nov. 29, 2001

Related U.S. Application Data

(60) Provisional application No. 60/183,150, filed on Feb. 17, 2000.

(51) Int. Cl.[7] .............................................. A61M 31/00
(52) U.S. Cl. ...................................... 604/506; 604/501
(58) Field of Search .............................. 604/21, 22, 28, 604/35, 36, 43, 174, 264, 164.01, 167.01, 167.06, 167.04, 501, 500, 506, 507, 508, 511; 128/898

(56) References Cited

U.S. PATENT DOCUMENTS

| | | | | |
|---|---|---|---|---|
| 4,423,740 A | * | 1/1984 | Castle et al. ................ | 600/561 |
| 4,692,153 A | * | 9/1987 | Berlin et al. ................ | 604/171 |
| 5,078,689 A | * | 1/1992 | Keller ................... | 604/167.02 |
| 5,484,399 A | * | 1/1996 | DiResta et al. ............. | 600/561 |
| 5,628,733 A | * | 5/1997 | Zinreich et al. ............ | 604/267 |
| 6,030,358 A | * | 2/2000 | Odland ....................... | 604/264 |

OTHER PUBLICATIONS

Journal of the National Cancer Institute, "New Cancer Statistics Show Losses, Gains", pp. 1238–1239.
Rakesh K. Jain, Cancer Research (Suppl.) 50, Feb. 1, 1990, "Physiological Barriers to Delivery of Monoclonal Antibodies and Other Macromolecules in Tumors", pp. 814s–819s.
Rakesh K. Jain, Cancer and Metastasis Reviews 9, 1990, "Vascular and Interstitial Barriers to Delivery of Therapeutic Agents in Tumors", pp. 253–266.
F. Hammersen, Microvasculature of Skeletal Muscle, "The Terminal Vascular Bed in Skeletal Muscle with Special Regard to the Problem of Shunts", pp. 351–365.

(List continued on next page.)

*Primary Examiner*—Manuel Mendez
*Assistant Examiner*—Mark Han
(74) *Attorney, Agent, or Firm*—Pennie & Edmonds LLP

(57) ABSTRACT

An apparatus, system, and method are provided for reducing interstitial fluid pressure in tissue, particularly in tumors. The apparatus includes an aspiration probe with at least one slit along its body to provide fluid communication between the aspiration probe and the tissue. Suction in the chamber of the aspiration probe generated by a suction source reduces the interstitial fluid pressure. Compared to prior art devices, the geometry of the slit of the aspiration probe is less likely to become blocked. The present invention also includes a cleaning obturator to unclog the slit and a blocking obturator to prevent accumulation of tissue in the aspiration probe chamber when suction is off. The blocking obturator can be made of a number of biocompatible materials, including a material impregnated with a pharmacological agent. In order to enhance delivery of the pharmacological agent or any drug, the present invention also includes a conducting obturator made of an electrically conductive material to serve as an electroporation electrode. In one embodiment, at least a portion of the aspiration probe is made of an electrically conductive material and serves as an electroporation electrode.

28 Claims, 4 Drawing Sheets

OTHER PUBLICATIONS

G. Hauck, Symposia Angiologica Santoriana, $3^{rd}$ int. Symp., Fribourg 1970, Part I, Angiologica 8: (108–132) (1971), "Physiology of the Microvascular System", pp. 236–260.

A.G. Ogston et al., Prog. Biophys. Molec. Biol., 1978, vol. 34, General Descriptions of Passive Transport of Neutral Solute and Solvent Through Membranes, pp. 197–217.

Glenn H. Algire et al., National Cancer Institute, Bethesda, MD., "Vascular Reactions of Normal and Malignant Tissues In Vivo. IV. The Effect of Peripheral Hypotension on Transplanted Tumors", pp. 399–421.

H.A. Eddy et al., Microvascular Research 6, (1973), "Development of the Vascular System in the Hamster Malignant Neurilemmoma", pp. 63–82.

A.G. Ide et al., Department of Medicine (Division of Radiology) of the University of Rochester, School of Medicine and Dentistry and the Strong Memorial Hospital, Rochester, New York, vol. 42, No. 6, "Vascularization of the Brown–Pearce Rabbit Epithelioma Transplant as Seen in the Transparent Ear Chamber", pp. 891–899.

W. Peters et al., Journal of the National Cancer Institute, vol. 65, No. 3, Sep. 1980, "Microcirculatory Studies in Rat Mammary Carcinoma I. Transparent Chamber Method, Development of Microvasculature, and Pressures in Tumor Vessels", pp. 631–637.

B.A. Warren, Microvascular Research 2, (1970), "The Ultrastructure of the Microcirculation at the Advancing Edge of Walker 256 Carcinoma", pp. 443–553.

H. Yamaura et al., Journal of the National Cancer Institute, vol. 53, No. 5, Nov. 1974, "Quantitative Studies on the Developing Vascular System of Rat Hepatoma", pp. 1229–1240.

T.P. Butler et al., Cancer Research, vol. 35, Mar. 1975, "Quantitation of Cell Shedding into Efferent Blood of Mammary Adenocarcinoma", pp. 512–516.

Rakesh K. Jain, Cancer Research 47, Jun. 15, 1987, "Transport of Molecules in the Tumor Interstitium: A Review", pp 3039–3051.

Rakesh K. Jain, Biotechnology Process, vol. 1, No. 2, Jun. 1985, "Transport of Macromolecules in Tumor Microcirculation", pp. 81–94.

K. Hori et al., Jpn. Journal of Cancer Research (Gann), 77, Jan. 1986, "Increased Tumor Tissue Pressure in Association with the Growth of Rat Tumors", pp. 65–73.

A. J. Paskins–Hurlburt et al., Microvascular Research 24, 1982, "Tumor Perfusion in Relation to the Rapid Growth Phase and Necrosis: Studies on the Walker Carcinoma in the Rat Testicle", pp. 15–24.

H. Wilg et al., Scand. J. Clin. Lab. Invest. 42, 1982, "Interstitial Fluid Pressure in DMBA–Induced Rat Mammary Tumours", pp. 159–164.

J.S. Young et al., Journal of Pathology and Bacteriology, vol. LXII, No. 3, "The Dynamics of Parenchymatous Embolism in Relation tot he Dissemination of Malignant Tumours", pp. 293–311, 13 sheets of drawings.

M. Intaglietta et al., American Journal of Physiology, vol. 221, No. 3, Sep. 1971, "Blood Pressure, Flow, and Elastic Properties in Microvessels of Cat Omentum", pp. 922–928.

R. K. Jain et al., Department of Chemical Engineering, Carnegie Mellon University, Pittsburgh, Pennsylvania, "Mechanisms of Heterogeneous Distribution of Monoclonal Antibodies and Other Macromolecules in Tumors: Significance of Elevated Interstitial Pressure", pp. 7022–7032.

L. T. Baxter et al., Microvascular Research 37, 1989, "Transport of Fluid and Macromolecules in Tumors I. Role of Interstitial Pressure and Convection", pp. 77–104.

Rakesh K. Jain, Journal of the National Cancer Institute, "Delivery of Novel Therapeutic Agents in Tumors: Physiological Barriers and Strategies", pp. 570–576.

Gene R. DiResta, $221^{st}$ National Meeting of the ACS, "Advances in Controlled Drug Delivery".

Gene R. DiResta et al., Annals of Biomedical Engineering, vol. 28, 2000, "Enhancing the Uptake of Chemotherapeutic Drugs into Tumors Using an 'Artificial Lymphatic System'", pp. 556–564.

Gene R. DiResta et al., Annals of Biomedical Engineering, vol. 28, 2000, "'Artificial Lymphatic System': A New Approach to Redue Interstitial Hypertension and Increase Blood Flow, pH and $pO_2$ in Solid Tumors", pp. 543–555.

* cited by examiner

APPARATUS AND METHOD FOR REDUCING INTERSTITIAL FLUID PRESSURE AND ENHANCING DELIVERY OF A THERAPEUTIC AGENT

CROSS-REFERENCE TO RELATED APPLICATIONS

The benefit of Provisional Application No. 60/183,150 filed on Feb. 17, 2000 is claimed under 35 U.S.C. § 119(e).

FIELD OF THE INVENTION

The present invention relates to an apparatus and method for reducing interstitial fluid pressure, enhancing radiation therapy, and enhancing delivery and effectiveness of therapeutic agents in tissue, particularly in tumors.

BACKGROUND OF THE INVENTION

Throughout this application various publications are referenced and citations are provided in the Reference section. The disclosure of these publications in their entireties are hereby incorporated by reference into this application in order to more fully describe the state of the art to which this invention pertains.

Cancer is the second leading cause of death in this country and still continues to be a public health problem of increasing significance.[1] Cancer therapy may be categorized into three major approaches: surgical excision, radiotherapy, and chemotherapy. Chemotherapy is defined as the treatment of cancer by a systemic administration of drugs.

Unfortunately, most drugs which showed promising effects in vitro have failed to be as effective in vivo, particularly in solid tumors. It has been proposed that one of the major reasons for this failure is the impediment of drug transport into tumors. In particular, a physiological barrier created by raised interstitial fluid pressure appears to be responsible. The interstitial fluid pressure is raised in tumors primarily because of the lack of lymphatics in tumors and growth of tumor cells in confined spaces. The raised interstitial fluid pressure in tumors is a principal transport-retarding factor for the delivery of drugs such as macromolecules, i.e., large molecular weight molecules such as monoclonal antibodies (MoAb), tumor necrosis factor, and other chemotherapeutic agents.

Jain et al. suspected that elevated interstitial fluid pressure is a principal transport retarding factor in MoAb delivery because of the lack of lymphatics in the tumor.[2,3] In normal tissue, maintenance of the fluid balance within the tissue spaces is dependent upon the interplay of hydrostatic and colloid osmotic pressures operating on a vascular network with uneven permeability and with dissimilar exchange area with the aid of the lymphatic system. The lymphatics are responsible for returning extravasated fluids and macromolecules to circulation throughout the body. Most macromolecules, including proteins, cannot return to circulation without the lymphatic system after they percolate through the endothelial wall.[4] Accordingly, lymphatic drainage is a factor of primary importance in maintaining fluid balance.[5] Once the equilibrium is disrupted, dehydration or edema in the tissue would result from the imbalanced colloid osmotic and hydrostatic vascular pressure. These relations are well described by Starling's hypothesis.[6]

A functioning lymphatic system as an anatomical entity has not been demonstrated in the tumor. The absence of lymphatics affords no alternative way by which macromolecules can re-enter the circulation after their extravasation through the capillaries. The potential of fluid flow into the tumor is hindered by an opposing force with equivalent magnitude from interstitial fluid pressure. This opposing force increases until all the forces in Starling's Law are balanced. The convective component of drug transport from capillary to interstitial space is blocked and the predominant mechanism is molecular diffusion. Fluid oozes out toward the tumor surface because of the lower effective pressure at the tumor periphery resulting from draining advantage by lymphatics of the normal tissue at the tumor periphery. This outward fluid velocity from the tumor center to the tumor periphery additionally hinders the diffusional movement of treatment molecules into the tumor center.[2] Decreased intravascular pressure and/or increased interstitial pressure in tumors has been demonstrated by several investigators.[7-12]

Findings to date indicate that elevated interstitial fluid pressure has been attributed to the absence of a well-defined lymphatic system in the tumor,[3,13] and to increased permeability of tumor vessels.[14,15] Researchers reported that interstitial fluid pressure increases with tumor size.[16-19] The increase in interstitial fluid pressure has also been shown to correlate with reduction in tumor blood flow (lower blood perfusion rate) and the development of necrosis in a growing tumor.[16-18,20]

Jain et al. presented a mathematical model describing the possible relationship between the distribution of macromolecules, e.g., monoclonal antibodies (MoAbs) and elevated interstitial pressure.[21] They proposed that increased interstitial fluid pressure might be responsible for the poor penetration of MoAbs into tumors including the heterogeneous blood perfusion, hindered diffusion in the interstitium, and extravascular binding of MoAbs. Furthermore, they stated that the elevated interstitial pressure principally reduces the driving force for extravasation of fluid and macromolecules in tumors, and leads to an experimentally verifiable, radially outward convection which opposed the inward diffusion. They have presented results from several mathematical models and the models' implications to support their hypothesis.[2,3,22,23]

A variety of approaches have been tried to enhance delivery of therapeutic agents to tumors. For example, U.S. Pat. No. 5,484,399 to DiResta et al. ("DiResta '399 patent"), the contents of which are incorporated herein by reference, discloses a process and device to reduce interstitial fluid pressure in tissue. Briefly, the DiResta '399 patent discloses an artificial lymphatic system (ALS) which includes a plurality of aspiration tubes, each having a plurality of aspiration holes, and a manifold for connecting the tubes to a vacuum source. Experimental studies have shown that the ALS has resulted in reduced interstitial fluid pressure within tumors, increased blood flow within tumors, and enhanced uptake of chemotherapeutic drugs into the tumors. Specifically, by reducing interstitial fluid pressure, blood flow, pH, and $pO_2$ all increase to more normal levels. These changes increase delivery of drugs to the tissue and drug uptake into the cells. The increase in tissue pH enhances the reaction kinetics of drugs whose pH optimum is in the normal range. Increasing $pO_2$ enhances radiation therapy because oxygen is the most potent radiationsensitizing agent currently known.

Despite these promising findings, there are limitations to the ALS. Specifically, the small holes in the ALS may tend to become blocked with time. As a result, long term use of the ALS could potentially be problematic. Long term use of the ALS may further be complicated by the lack of a mechanism to secure the drains of the ALS to the tissue so that the drains remain spatially fixed. Finally, the ALS had no features that facilitate use with adjunct therapies that enhance drug delivery. Use of various other therapies to enhance efficacy of the ALS would be desirable. However, until now, no other adjunct therapy has been used in conjunction with the ALS.

Electroporation is another therapy that has been used to enhance delivery of therapeutic agents to tumors. Recent studies have demonstrated that electroporation may be beneficial in the treatment of accessible solid tumors. Electroporation is a technique that uses pulsed electric fields to create transient pores within cell membranes to temporarily increase the membrane's permeability to exogenous molecular agents. The electric fields are created between pairs of needle electrodes inserted into a tissue region of interest. The electrode separation distance is typically fixed and a grid array of electrodes is used to treat tissue regions.

As electroporation requires that the desired drugs be within the tissue region to be treated when the electric field is induced, the major problem with the successful use of electroporation is the need for an adequate quantity of the therapeutic agent in the region at which the electric field will be generated. Blood flow is low in many solid tumors and thus drugs administered via intravenous or intra-arterial routes frequently do not enter the tumor in cytotoxic concentrations. As an alternative, intra-tumoral injections are used to deliver the drugs directly into the tumor regions scheduled for electroporation to avoid the transport problems. However, the drug distribution from intra-tumoral injection is non-uniform and the technique requires multiple injections with fan motions that may damage the tissue.

As previously indicated, low tumor blood flow results from the existence of elevated interstitial fluid pressure within the tumor. The physiological basis cited to explain this phenomena includes the tumor's "leaky" capillaries and lack of a functioning lymphatic system to drain the excess fluid that accumulates within the interstitial spaces. The elevated interstitial fluid pressure throttles the blood flow that delivers drug to tumors. In addition, the elevated interstitial fluid pressure reduces the convective component of drug movement from the capillaries into the interstitial spaces. As a result, drug movement proceeds via diffusion, a much slower process. It would be advantageous to use a system, such as the ALS, in conjunction with electroporation so that drug delivery is enhanced. However, as the ALS was not designed for use with electroporation, their simultaneous use is not straightforward.

Thus, there exists a need for an improved apparatus and process for reducing interstitial fluid pressure and enhancing delivery of a therapeutic agent.

SUMMARY OF THE INVENTION

The present invention relates to an interstitial fluid pressure reducing apparatus that includes an aspiration probe having a body with an open proximal end and a closed distal end, an interior chamber defined by the body and proximal and distal ends, and at least one slit along the body providing fluid communication between the chamber of the aspiration probe and tissue upon insertion of at least a portion of the aspiration probe in tissue. The proximal end is configured and dimensioned for coupling to a suction source for generating suction in the chamber of the aspiration probe upon connection with the aspiration probe to thereby reduce interstitial fluid pressure of the tissue.

In order to secure the aspiration probe to tissue, the aspiration probe can have a suture ring at the proximal end. In one embodiment, at least one hole is defined in the suture ring shaped to receive a suture. The apparatus can include a connection member having a first end configured and dimensioned for removably connecting with the proximal end of the aspiration probe and a second end configured and dimensioned for removably connecting with the suction source.

The apparatus optionally includes other components. One such component is a cleaning obturator configured and dimensioned for sliding movement into the chamber through the proximal end of the aspiration probe. The cleaning obturator has at least one fin engaging at least one slit upon insertion of the cleaning obturator into the chamber for removing any debris from the slit.

A blocking obturator can also be a component of the apparatus. The blocking obturator is configured and dimensioned to fit within the chamber to block at least one slit. As a result, fluid communication between the chamber of the aspiration probe and tissue is blocked to prevent accumulation of tissue or debris in the chamber. The blocking obturator can have at least one rib configured and dimensioned to block at least one slit.

The apparatus can also include a conducting obturator configured and dimensioned for sliding movement into the chamber. The conducting obturator is made of an electrically conductive material for serving as an electrode for electroporation. In one embodiment, at least a portion of the aspiration probe is made of an electrically conductive material for serving as an electrode for electroporation.

The present invention also relates to an interstitial fluid pressure reducing apparatus comprising an aspiration probe having a body with an open proximal end and a closed distal end, an interior chamber defined by the body and proximal and distal ends, and a plurality of apertures along the body providing fluid communication between the chamber of the aspiration probe and tissue upon insertion of at least a portion of the aspiration probe in tissue. The proximal end is configured and dimensioned for coupling with a suction source for generating suction in the chamber of the aspiration probe upon connection with the aspiration probe to thereby reduce interstitial fluid pressure of the tissue. The apparatus further comprises a cleaning obturator configured and dimensioned for sliding movement into the chamber through the proximal end of the aspiration probe. The cleaning obturator has at least one protrusion engaging the plurality of apertures upon insertion of the cleaning obturator into the chamber for removing any debris from the plurality of apertures.

The present invention also relates to an interstitial fluid pressure reducing apparatus comprising an aspiration probe having a body with an open proximal end and a closed distal end, an interior chamber defined by the body and proximal and distal ends, and a plurality of apertures along the body providing fluid communication between the chamber of the aspiration probe and tissue upon insertion of at least a portion of the aspiration probe in tissue. The proximal end is configured and dimensioned for coupling with a suction source for generating suction in the chamber of the aspiration probe upon connection with the aspiration probe to thereby reduce interstitial fluid pressure of the tissue. The apparatus further comprises a blocking obturator configured and dimensioned to fit within the chamber to block the plurality of apertures thereby blocking the fluid communication between the chamber of the aspiration probe and tissue for preventing accumulation of tissue or debris in the chamber. The blocking obturator can be impregnated with a therapeutically effective amount of a pharmacological agent, such as an antibiotic. In one embodiment, the blocking obturator is made of a biocompatible polymer, such as polymethyl methacrylate. At least a portion of the blocking obturator can be made of an electrically conductive material for serving as an electrode for electroporation.

The present invention also relates to a system for reducing interstitial pressure of tissue. The system comprises at least two aspiration probes, each having a body with an open proximal end and a closed distal end, an interior chamber defined by the body and proximal and distal ends, and at least one slit along the body providing fluid communication between the chamber of the aspiration probe and tissue upon insertion of at least a portion of the aspiration probe in tissue. A suction source generates suction in the chamber of each of the aspiration probes upon connection with the respective aspiration probe to thereby reduce interstitial fluid pressure of the tissue. The system also includes a plurality of connection members, each having a first end configured and dimensioned for removably connecting with the proximal end of one of the aspiration probes and a second end configured and dimensioned for removably connecting with the suction source. A manifold having a suction source port removably connects with the suction source and a plurality of aspiration probe ports, each for removably connecting with one of the connection members. Each of the aspiration probes can have a separately adjustable vacuum pressure.

The system can include a chamber defined in the manifold in fluid communication with each of the aspiration probe ports for collection of aspirated fluid. The system can also include a valve operatively associated with each of the aspiration probe ports for selective coupling and uncoupling of the aspiration probe port to the suction source. A plurality of chambers can be defined in the manifold. Each chamber is in fluid communication with one of the aspiration probe ports for collection of aspirated fluid. Additionally, a valve is operatively associated with the suction source port for selective coupling and uncoupling to the suction source. The valve allows retention of pressure generated by the suction source upon uncoupling with the suction source. In this embodiment, at least a portion of the manifold can be implantable. The system can optionally include other components such as a cleaning obturator configured and dimensioned for sliding movement into the chamber through the proximal end of one of the aspiration probe. The cleaning obturator has at least one fin engaging at least one slit upon insertion of the cleaning obturator into the chamber for removing any debris from the slit. The system can also include at least one drug delivery probe having a body with an open proximal end and a closed distal end, an interior chamber defined by the body and proximal and distal ends, and at least one slit along the body providing fluid communication between the chamber of the drug delivery probe and tissue upon insertion of at least a portion of the drug delivery probe in tissue. At least a portion of at least one of the aspiration probes can be made of an electrically conductive material for serving as an electrode for electroporation.

The present invention also relates to a method for reducing interstitial fluid pressure of tissue comprising the steps of: implanting at least a portion of an aspiration probe in tissue; coupling the aspiration probe to a suction source to generate suction in the aspiration probe and thereby reduce interstitial fluid pressure of tissue; and cleaning the aspiration probe to remove debris. At least a portion of the aspiration probe remains implanted in tissue when the aspiration probe is cleaned. The method can also include the step of inserting a blocking obturator in the aspiration probe when suction is not applied to prevent debris from accumulating in the aspiration probe. Furthermore, the suction source can selectively be turned on and off or adjusted to different levels to generate a pressure field to assist in delivery and distribution of a pharmacological agent to tissue regions.

The present invention also relates to another method for reducing interstitial fluid pressure of tissue. At least a portion of at least two aspiration probes is implanted in tissue. At least one of the aspiration probes is coupled to a suction source to generate suction and thereby reduce interstitial fluid pressure of tissue. Drug is delivered to the tissue and the delivery of the drug is assisted with electroporation. At least a portion of at least one of the aspiration probes is made of electrically conductive material for serving as an electrode for the electroporation. In one embodiment, suction and electroporation occur simultaneously.

DETAILED DESCRIPTION OF THE PREFERRED EMBODIMENTS

Figure 1:
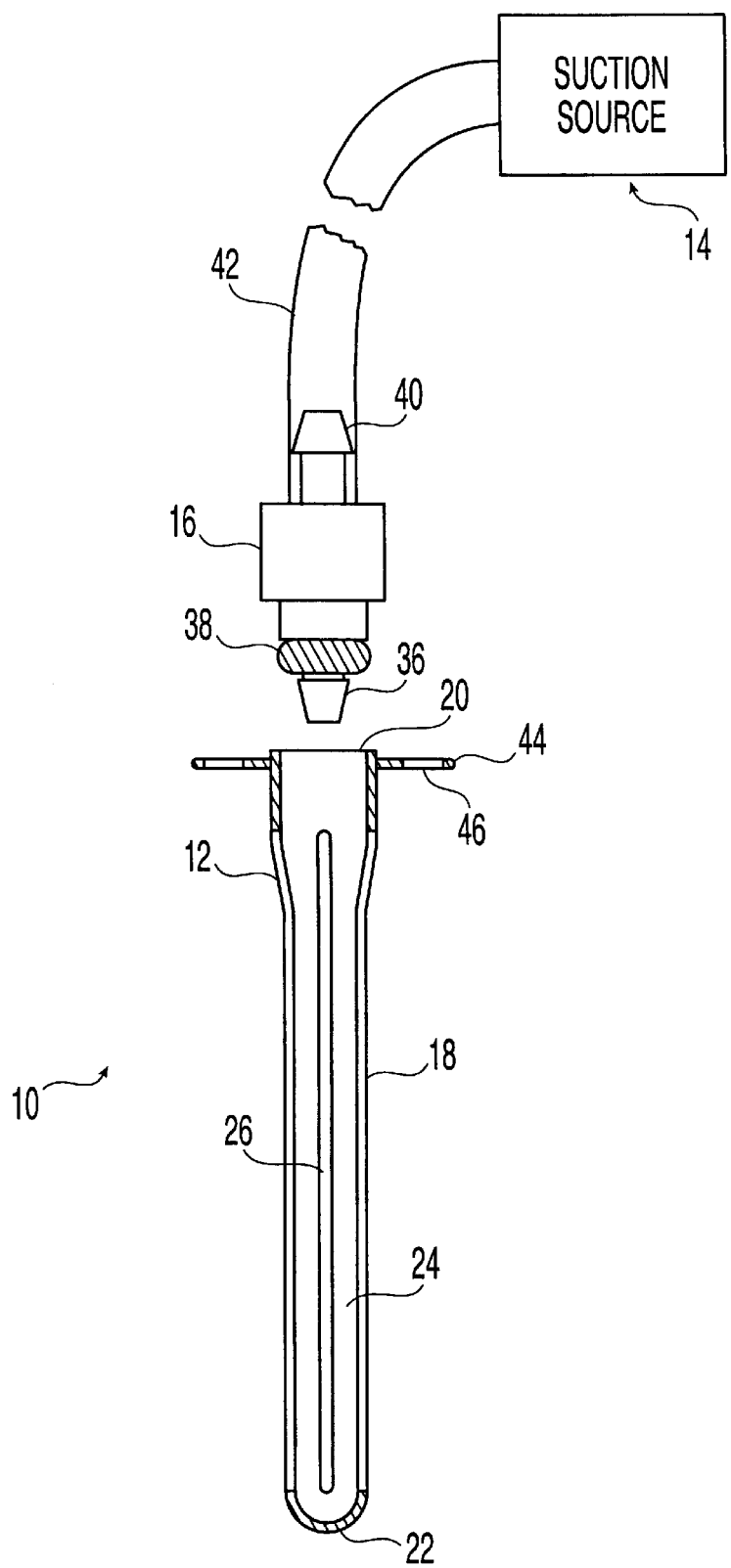
FIG. 1 is a side view of an aspiration probe and connection member according to the present invention with a suction source shown in schematic form.

FIG. 1 shows a treatment apparatus 10 according to the present invention used for a number of therapies, including, but not limited to, reducing interstitial fluid pressure, delivery of a pharmacological agent, and electroporation. As used for reducing interstitial fluid pressure, apparatus 10 has an aspiration probe 12 for establishing fluid communication between apparatus 10 and the tissue to be treated, a suction source 14 for generating suction in aspiration probe 12 to thereby reduce interstitial fluid pressure of the tissue into which aspiration probe 12 is inserted, and a connection member 16 for connecting aspiration probe 12 to suction source 14.

Aspiration probe 12 has a body 18 with an open proximal end 20 and a closed distal end 22. Proximal end 20 can be configured for direct connection to suction source 14, thereby eliminating the need for a separate connection member 16. Closed distal end 22 can be rounded as shown in FIG. 1. Alternatively, distal end 22 can have a sharp tip or any other suitable configuration. An interior chamber 24 is defined by body 18 and proximal and distal ends 20, 22. The exterior of body 18 can be threaded to facilitate insertion. In this regard, distal end 22 can be in the form of a self-tapping, self-drilling tip to eliminate the need to drill a pilot hole in hard tissue, e.g., bone. Body 18 has at least one aperture 26 running along its length for providing the fluid communication between chamber 24 and the tissue being treated upon insertion of at least a portion of aspiration probe 12 in the tissue.

Aspiration probe 12 can be made of a wide variety of biocompatible materials. Examples include a surgical grade stainless steel (such as 316L), titanium, a titanium based alloy, polymers, and ceramics. Polymers or ceramics would be useful for minimizing scatter if radiation therapy is anticipated. Ceramics with plated electronic circuits serving as biosensors for measuring pressure, temperature, pH, or other environmental parameters are also contemplated by the present invention. If aspiration probe 12 is made of an electrically conductive material, aspiration probe 12 can also serve as an electrode for electroporation, a treatment discussed in further detail below. A second aspiration probe 12 or a needle electrode serves as the second electrode to complete the electrode pair for generating an electric field in the tissue in which aspiration probe 12 is inserted.

The shape, size, number, positioning, and other parameters of aperture 26 can be varied to create the desired clinical affect. For instance, aperture 26 may be in the form of a slit, and four identical slits may be symmetrically placed on body 18. However, other shapes, such as those disclosed in U.S. Pat. No. 5,484,399 to DiResta et al., which is hereby incorporated by reference in its entirety, may be used instead. If apertures 26 are in the form of slits, the slits preferably are elongated, such shape being less susceptible to becoming blocked with biological material than other shapes, such as smaller apertures. In particular, when small apertures are used with bone tumors, such as an osteogenic sarcoma, a friable, gritty matrix blocks the small apertures so that there is little or no reduction of interstitial fluid pressure. An elongated slit geometry, such as the one shown in FIG. 1, overcomes this problem. For instance, it is unlikely that any single particle will block the slit.

Figure 2:
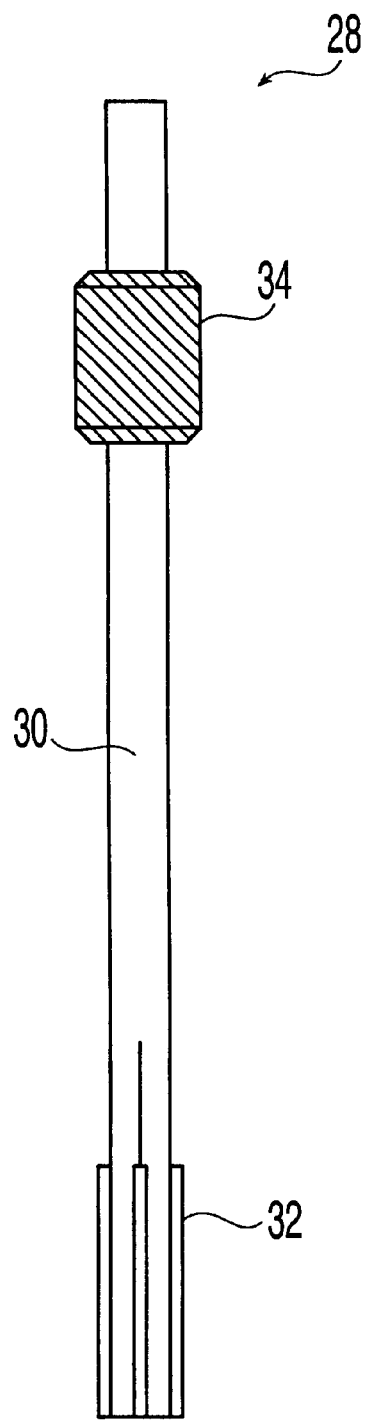
FIG. 2 is a side view of a cleaning obturator according to the present invention.

Furthermore, if slit 26 does becomes blocked, an elongated slit permits simplified cleaning. In this regard in accordance with the principles of the present invention, apparatus 10 preferably includes a cleaning obturator 28 for removing any trapped material from slit 26. An exemplary embodiment of cleaning obturator 28 is shown in FIG. 2. Cleaning obturator 28 has a shaft 30 sized to slide into interior chamber 24 of probe 12, and is provided with an arrangement of fins 32 corresponding to the arrangement of slits 26 on body 18 of aspiration probe 12. As cleaning obturator 28 is slid into chamber 24, fins 32 engage slits 26 to remove any debris from slits 26. Proximal end 34 of cleaning obturator 28 is preferably shaped to facilitate handling of cleaning obturator 28. In order to further enhance the cleaning ability of cleaning obturator 28, shaft 30 can be hollow so that fluid flow from a syringe or other source may be imparted to act as a lavage to rinse interior chamber 24. Alternatively, the hollow shaft 30 can be connected to a suction source so that debris within aspiration probe 12 is suctioned out as slits 26 are cleaned.

In order to use cleaning obturator 28, aspiration probe 12 is removed from suction source 14 by disconnecting connection member 16 from aspiration probe 12. Specifically, a first end 36 of connection member 16, which is configured and dimensioned for removably connecting with proximal end 20 of aspiration probe 12, is pulled from proximal end 20. First end 36 has a seal 38, such as an O-ring or a similar element, for creating a fluid-tight seal between aspiration probe 12 and connection member 16. A second end 40 of connection member 16 is also preferably removably coupled to tubing 42, which leads to suction source 14.

It will be appreciated that cleaning obturator 28 preferably is shaped to effect the desired cleaning of apertures 26. For example, if apertures 26 are elongated slits, fins 32 extend through the slits and serve to push out any debris that may have entered. It should be noted that fins 32 need not extend the entire length of the elongated slits. If apertures 26 have a shape other than an elongated slit, cleaning obturator 28 can have an appropriate configuration. An example of such a configuration is providing cleaning obturator 28 with bristles. Regardless of the specific configuration of cleaning obturator 28, rotation of cleaning obturator as it is inserted in aspiration probe 12 creates a small well to minimize blockage of apertures 26 associated with direct contact with adjacent tissue. Thus, cleaning obturator 28 allows in situ cleaning of aspiration probe 12, thereby permitting long term use of aspiration probe 12.

At least a portion of aspiration probe 12 is inserted in the tissue to be treated so that interstitial fluid pressure can be reduced in the tissue by apparatus 10. In one embodiment, substantially all of aspiration probe 12 is implanted to minimize patient discomfort. Aspiration probe 12 may be provided with a fastening element to facilitate fastening of probe 12 at the treatment site. For example, a suture ring 44 with at least one hole 46 for receiving a suture or other fastener may be provided so that the implantation location of aspiration probe 12 remains constant.

Figure 3:
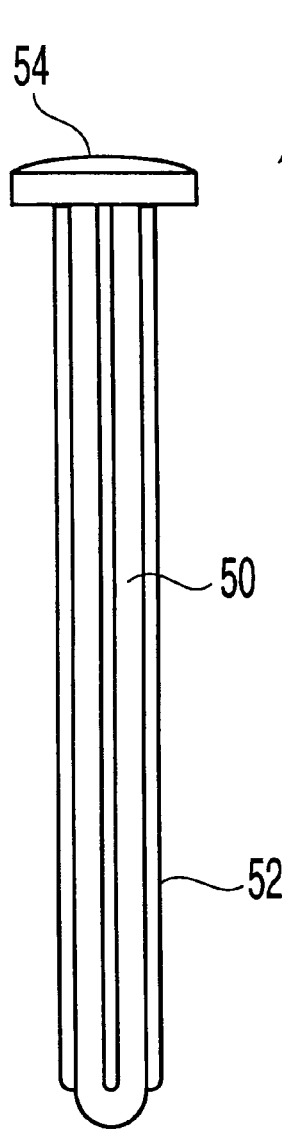
FIG. 3 is a side view of a blocking obturator according to the present invention.

FIG. 3 shows a blocking obturator 48 that prevents or reduces accumulation of tissue in slits 26 when aspiration probe 12 is not connected to suction source 14. Blocking obturator 48 has a shaft 50 sized to snugly slide into interior chamber 24. Preferably, shaft 50 is provided with an arrangement of elements sized and shaped to mate with apertures 26 of probe body 18. In the embodiment of FIGS. 1 and 3, blocking obturator shaft 50 is provided with ribs 52 configured to correspond to slits 26 on body 18 of aspiration probe 12. As blocking obturator 48 is slid into chamber 24, ribs 52 engage slits 26 to block fluid communication between chamber 24 and the tissue. Eliminating or at least partially restricting this fluid communication between chamber 24 and the tissue minimizes the chances that tissue can get trapped in slits 26. The potential for trapped tissue can result from different phenomena, including debris or tissue growth into slits 26. A distal end 54 of blocking obturator 48 is shaped to facilitate handling of blocking obturator 48.

Although blocking obturator 48 can be made of any biocompatible material, if blocking obturator 48 is made of metal, it is preferably made of the same metal as aspirating probe 12 to prevent mixed metal (galvanic) corrosion. If blocking obturator 48 is made of an electrically conductive material, blocking obturator 48 can also serve as an electrode for electroporation. A blocking obturator 48 which is formed of a material impregnated with a desired agent may be provided to serve an additional function of providing a slow, controlled release of the agent. There are a number of biocompatible materials, such as polymethyl methacrylate, nylon, and a porous inorganic matrix (e.g., a ceramic), that can be impregnated with pharmacological agent and used to make blocking obturator 48. Examples of agents include antibiotics for preventing infections around aspiration probe 12 and chemotherapeutics for treating tumors. Blocking obturator 48 can be impregnated with a combination of these agents. As an alternative drug delivery modality, aspiration probe 12 can be used to deliver a bolus of a pharmacological agents through slits 26 when connection member 16 is coupled to a delivery device, such as a syringe. Such a bolus delivery can be advantageous when a plurality of aspiration probes 12 are used in treatment, as described in more detail below.

Figure 4:
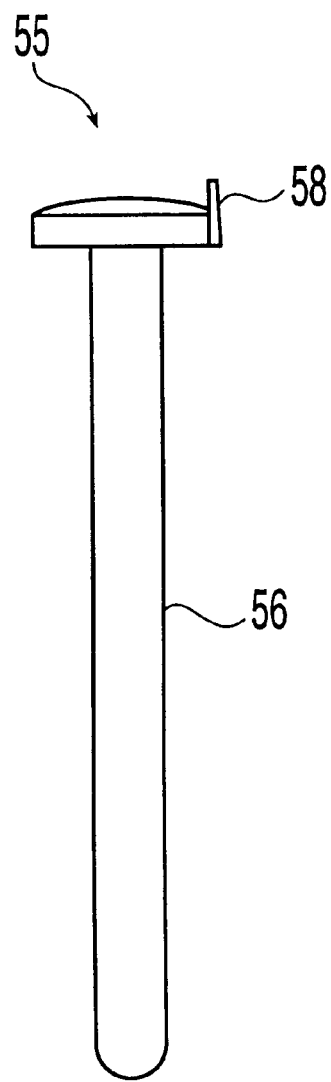
FIG. 4 is a side view of a conducting obturator according to the present invention.

A third obturator, a conducting obturator 55, may be provided for use with aspiration probe 12. An exemplary conducting obturator 55 is shown in FIG. 4. Conducting obturator 55 has a shaft 56 sized for sliding into interior chamber 24 of aspirating probe 12 and is made of an electrically conductive material. Conducting obturator 55 has a fitting 58 for connection to an electroporation device. Thus, conducting obturator 55 serves as an electrode for generating an electric field in the tissue. Conducting obturator 55 may be provided with protrusions that fit in apertures 26 of aspiration probe 12. These protrusions increase contact between the tissue and conducting obturator 55. A second conducting obturator 55 inserted in a second aspiration probe 12, an aspiration probe 12 made of an electrically conducting material, or a needle electrode can serve as the second electrode to complete the electrode pair. These electrodes are placed in the tissue so that when the electrical fields are activated, the entire tissue region targeted for treatment receives a uniform electric field. This promotes a more uniform distribution of any agent in the tissue.

Now that basic structural elements of apparatus 10 have been described with reference to certain exemplary embodiments, use of apparatus 10 will now be described. When aspiration probe 12 is connected to an active suction source 14, suction is generated in interior chamber 24 and also in the tissue in which probe 12 is inserted through the fluid communication created by apertures 26. Aspiration of the treatment site reduces interstitial fluid pressure in the tissue and increases blood flow to improve delivery of drugs as described in the incorporated DiResta '399 patent. When aspiration probe 12 is disconnected from suction source 14, a cleaning obturator 28 can be used to remove any debris from apertures 26. Additionally, a blocking obturator 48 may be fitted into chamber 24 to help prevent accumulation of debris or tissue ingrowth in apertures 26. If blocking obturator 48 is made of a material impregnated with pharmacological agent(s), blocking obturator 48 also serves as a slow release delivery mechanism for the agent(s). Alternatively, a bolus injection of the agent(s) can be delivered through aspiration probe 12 itself. If the tissue to be treated is particularly poorly vascularized, such as is the case with a tumor, conducting obturator 55 may be used to serve as an electrode for electroporation to enhance uptake of the agent(s) into tumor cells. Alternatively, aspiration probe 12 can be formed of an electrically conductive material and serve a dual function as an aspiration probe as well as an electrode for electroporation. It should be noted that aspiration and electroporation can occur simultaneously.

Figure 5:
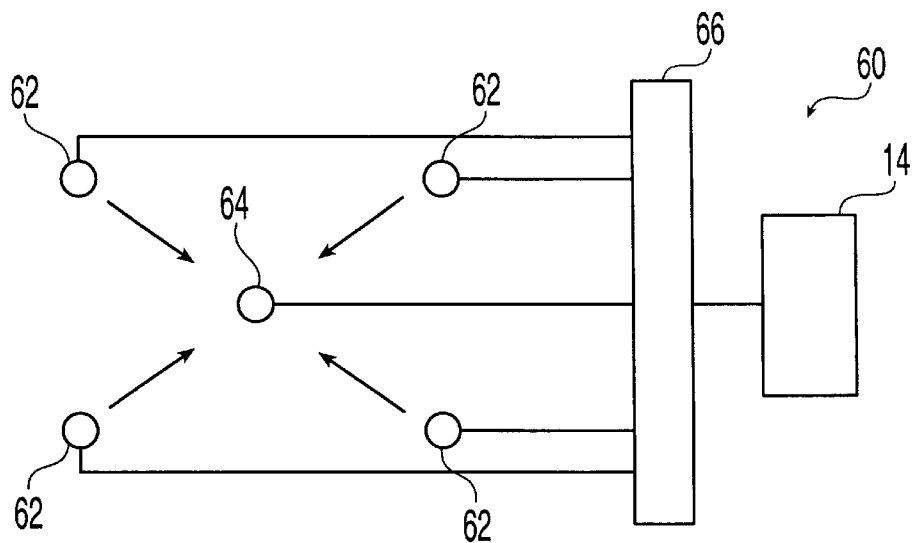
FIG. 5 is a schematic view of a system for reducing interstitial fluid pressure according to the present invention.

As shown in FIG. 5, in accordance with the general principles of the present invention, a system 60 for reducing interstitial pressure of tissue may be provided. System 60 includes a plurality of aspiration probes 62, 64, suction source 14, a plurality of connection members, which are in any desired form permitting connection of aspiration probes 62, 64 to suction source 14 (such as the form of connection members 16), and a manifold 66. In general, most of the structure of aspiration probes 62, 64 is like or comparable to the structure of aspiration probe 12 and, accordingly, the same reference numeral is used for like components and discussion of those like components is not believed necessary, reference being made to the previous description of such components. The number of aspiration probes 62, 64 and the spatial positioning of the probes is dependent on the tissue (e.g., tissue size, shape, type, etc.) as well as the intended therapeutic treatment.

Figure 6:
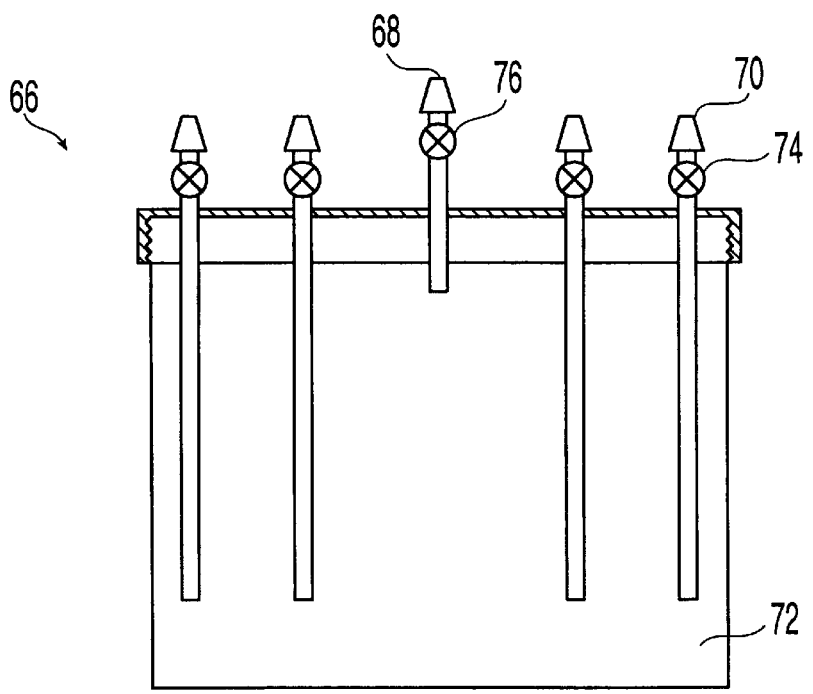
FIG. 6 is a manifold according to the present invention.

FIG. 6 shows one embodiment of manifold 66. Manifold 66 has a suction source port 68 for removable coupling with suction source 14 and a plurality of aspiration probe ports 70 for removable coupling with connection members 16. Manifold 66 has a sampling chamber 72 in fluid communication with each of aspiration probe ports 70 for collection of aspirated fluid. Manifold 66 can also have a plurality of sampling chambers, i.e., one sampling chamber for each of aspiration probe ports 70, so that only aspirated fluid from selected aspiration probe ports 70 is sampled. The selective sampling can be useful for testing specific sites in the tissue being treated. Each of aspiration probe ports 70 has an associated valve 74 for selective control and/or coupling and uncoupling of one of aspiration probe ports 70 to suction source 14. The selective control and/or coupling and uncoupling provided by valve 74 allows different degrees of aspiration at different probe sites, i.e., each probe can have its own vacuum pressure, and also allows one of aspiration probes 62, 64 to be disconnected from suction source 14, while the others are still connected to suction source 14. Valve 74 can be located any where between aspiration probe port 70 and connection member 16. The different degrees of aspiration at different probe sites can be useful for various therapeutic effects such as relief of a pressure imbalance and generation of a particular interstitial fluid pressure gradient in the tissue.

If valve 74 of aspiration probe port 70 for aspiration probe 64 is completely closed, aspiration probe 64 is uncoupled from suction source 14. As a result, cleaning obturator 28 can be used to clean aspiration probe 64 while aspiration probes 62 are still operatively coupled to suction source 14. Another benefit of having valve 74 closed would be if blocking obturators 48 loaded with a pharmacological agent are inserted or drug injected in aspiration probes 62 with valves 74 for aspiration probe ports 70 of aspiration probes 62 closed. If negative pressure, i.e., suction, is present in aspiration probe port 70 for aspiration probe 64, then the created field of lower pressure surrounding aspiration probe 64 (compared to the field of pressure around aspiration probes 62) will cause fluid movement towards aspiration probe 64, as indicated by the arrows. The fluid flow thus generated will result in enhanced delivery of the pharmacological agents. The direction and rate of fluid motion depends upon placement of aspiration probes 62, 64, suction level and duration, tissue properties, and the number and location of aspiration probes 62, 64 that receive blocking obturators 48. It therefore will be appreciated that a blocking obturator 48 may be placed in one or more of the probes at the treatment site and vacuum may be applied to any probe in which a blocking obturator has not been placed to generate any desired flow path to effect the desired delivery of pharmacological agents.

Suction source port 68 can be provided with a suction valve 76 for selective control and/or coupling and uncoupling to suction source 14. Suction valve 76 can be located any where between suction source portion 68 and suction source 14. Control of suction valve 76 allows the user to select the desired level of suction applied. Suction valve 76 allows retention of the pressure generated by suction source 14 upon uncoupling with suction source 14 such as by storing the negative pressure created by suction source 14 in manifold 66 after closing suction valve 76. As a result of this pressure retention, manifold 66 acts like a "suction battery", retaining a stored level of vacuum until application of vacuum is desired. When any of aspiration valves 74 are opened, the stored vacuum pressure is applied to achieve aspiration and vacuum pressure is thereby reduced as aspirated fluid moves into manifold 66. This suction battery is passive, implantable, and rechargeable.

In use, the plurality of aspiration probes 12, 62, 64, placed within the tissue region to be treated, provide an alternative drainage path for accumulated fluid in the tissue. A negative pressure, supplied to aspiration probes 12, 62, 64 by suction source 14, draws the accumulated fluid out of the tissue reducing interstitial fluid pressure. By reducing interstitial fluid pressure, blood flow, pH, and $pO_2$ all increase to more normal levels. These changes increase delivery of drugs to the tissue and drug uptake into the cells. In particular, the increase in tissue pH will enhance the reaction kinetics of drugs whose pH optimum is in the normal range. If the tissue is a tumor, increasing $pO_2$ will enhance radiation therapy because oxygen is the most potent radiation-sensitizing agent currently known.

After aspiration probes 12, 62, 64 are used to reduce interstitial fluid pressure and increase blood flow, selected aspiration probes 12, 62, 64 are removed from suction source 14 and blocking obturators 48 impregnated with pharmacological agents may be inserted in the interior chambers 24 of the selected aspiration probes 12, 62, 64. Negative pressure may be generated by selected aspiration probes 12, 62, 64 still coupled to suction source 14 to enhance delivery of the agent. The determination to end aspiration via suction source 14 can be made based on a number of factors, including: a predetermined time such as a set treatment time; measurements from a sensor located in the tissue (the sensor can be on one of the aspiration probes 12, 62, 64); and/or visual observation of a dye substance included as one of the pharmacological agents within the aspirated fluid. After aspiration is terminated, aspiration probes 12, 62, 64 which had applied suction can now be loaded with blocking obturators 48 to prohibit accumulation of debris or tissue growth in slits 26. The use of blocking obturators 48 minimizes exposure of the treated tissue and thereby reduces the potential for infection. Cleaning obturator 28 may be used to remove any accumulated debris or tissue. Furthermore, electroporation may be applied to drive the pharmacological agent into the cells. If the aspiration probes are made of a conductive material, then some or all of aspiration probes 12, 62, 64 may serve an additional function as electroporation electrodes. Alternatively, or in addition, conducting obturator 54 is used for an electroporation electrode.

EXAMPLE

The efficacy of the present invention has been demonstrated by the following example.

A system formed in accordance with the principles of the present invention was implanted in two dogs with limb osteogenic sarcomas prior to amputation of the effected limb. Aspiration probes made of 316 L stainless steel and having a length of 2 and 3 cm were implanted and connected to a manifold with tygon tubing. Both the lengths and diameters of the probes were selected based on the tissue region being treated. The number of probes used for each dog was determined by the surgeon. Probe positioning was determined using planar x-ray films. It should be noted that other techniques and instrument, such as MRI or CT scans, can be used for probe positioning. The mid-section of the tumor was selected for probe placement. The probes were inserted 1–2 cm apart using an insertion trochar.

In the first dog, five probes were inserted in a diamond-shaped pattern (four probes on the perimeter and a probe in the center). In the second dog, four probes were inserted in a square pattern. Interstitial fluid pressure (IFP) in the region was measured using the wickin-needle (WIN) technique and blood flow rate (BFR) was measured using laser Doppler flowmetry (LDF). Both of these techniques are well-known and described in detail in the incorporated DiResta '399 patent. Data acquisition started after connecting the manifold to a house vacuum (approximately 100 mmHg) and continued for a period of approximately 30 minutes. During the evaluation period, the house vacuum was turned off when IFP and BFR stabilized. The vacuum was turned on again after IFP and BFR values re-stabilized. This resulted in two or three cycles of vacuum on/vacuum off during the evaluation period.

The data recorded from both dogs showed that IFP was reduced when vacuum was applied to the aspiration probes and increased when vacuum was removed. For example, the IFP for the first dog decreased from 49 mmHg to 21 mmHg when the vacuum was on and returned to a level of 45 mmHg when the vacuum was turned back off. A cleaning obturator was used with the second dog and a recorded decrease in IFP after its use (from 4.9 mmHg to −82.6 mmHg) confirmed the ability of the cleaning obturator to unclog the aspiration probes. The LDF recordings show that flow generally increased during application of the vacuum.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

REFERENCES

1. Newman, M. E. New Cancer Statistics Show Losses, Gains. J. Nat'l. Cancer Inst. 82(15): 1238–1239, 1990.
2. Jain, R. K. Physiological Barriers to Delivery of Monoclonal Antibodies and Other Macromolecules in Tumors. Cancer Res. (Suppl.), 50: 814s-819s, 1990.
3. Jain, R. K. Vascular and Interstitial Barriers to Delivery of Therapeutic Agents in Tumors. Cancer and Metas. Rev., 9: 253–266, 1990.
4. Hammersen, F. The Terminal Vascular Bed in Skeletal Muscle with Special Regard to the Problem of Shunts, in: Capillary Permeability, Crone, C., Lassen, N. A., eds. Academic Press, 351–365, 1970.
5. Hauck, G. Physiology of the microvascular system. Angiologica 8:236–260, 1971.
6. Ogston, A. G., Michel, C. C. General Descriptions of Passive Transport of Neutral Solute and Solvent Through Membranes. Prog. Biophys. Mol. Biol. 34: 197–217, 1978.
7. Algire, G. H., Legallais, F. Y., Vascular Reactions of Normal and Malignant Tissues In Vivo, IV. The Effect of Peripheral Hypotension on Transplanted Tumors. J. Nat'l. Cancer Inst. 12: 399–421, 1951
8. Eddy, H. A., Casarett, G. W. Development of the Vascular System in the Hamster Malignant Neurilemmoma. Microvasc. Res. 6: 63–82, 1973.
9. Ide, A. D., Baker, N. H., Warren, S. H. Vascularization of the Brown-Pearce Rabbit Epithelioma Transplant as Seen in the Transparent Ear Chamber. Am. J. Roentgenol. 42: 891–899, 1939.
10. Peters, W., Teixeira, M., Intaglietta, M., Gross, J. F. Microcirculatory Studies in Rat Mammary Carcinoma, I. Transport Chamber Method, Development of Microvasculature and Pressures in Tumor Vessels. J. Nat'l. Cancer Inst. 65: 631–642, 1980.
11. Warren, B. A. The Ultrastructure of the Microcirculation of the Advancing Edge of Walker 256 Carcinoma. Microvasc. Res., 2: 443–453, 1970.
12. Yamaura, H., Sato, H. Quantitative Studies on the Developing Vascular System of Rat Hepatoma. J. Nat'l. Cancer Inst. 53: 1229–1240, 1974.
13. Butler, T. P., Grantham, F. H., Gullino, P. M. Bulk Transfer of Fluid in the Interstitial Compartment of Mammary Tumors. Cancer Res. 35: 512–516, 1975.

14. Jain, R. K. Transport of Molecules in the Tumor Interstitium: A Review. Cancer Res., 47: 3039–3051, 1987.
15. Jain, R. K. Transport of Macromolecules in Tumor Micro-Circulation. Biotechnol. Prog., 1: 81–94, 1985.
16. Hori, K., Suzuki, M., Abe, I., Saito, S. Increased Tumor Pressure in Association With the Growth of Rat Tumors. Japan J. Cancer Res. (Gann) 77:65–73, 1986.
17. Paskins-Hurlbart, A. J., Hollenberg, N. K., Abrams, H. L. Tumor Perfusion in Relation to the Rapid Growth Phase and Necrosis, Studies on the Walker Carcinoma in the Rat Testicle. Microv. Res. 24: 15–24, 1982.
18. Wiig, H., Tveit, E., Hultbom, R., Reed, R. K., Weiss, L. Interstitial Fluid Pressure in DMBA—Induced Rat Mammary Tumors. Scand. J. Clin. Lab. Invest., 42: 159–164, 1982
19. Young, J. S., Griffith, H. D. The Dynamics of Parenchymatous Embolism in Relation to the Dissemination of Malignant Tumors. J. Pathol. Bacteriol., 62: 293–311, 1950.
20. Intaglietta, M., Richardson, D. R., Tompkins, W.R. Blood Pressure, Flow, and Elastic Properties of Microvessels of Cat Omentum. Am. J. Physiol., 221: 922–928, 1971.
21. Jain, R. K., Baxter, L. T. Mechanisms of Heterogeneous Distribution of Monoclonal Antibodies and Other Macromolecules in Tumors: Significance of Elevated Interstitial Pressure. Cancer Res., 48: 7022–7032, 1988.
22. Baxter, L. T., Jain, R. K., Transport of Fluid and Macromolecules in Tumors: I. Role of Interstitial Pressure and Convection. Microvas. Res. 37:77–104, 1989.
23. Jain, R. K. Commentary: Delivery of Novel Therapeutic Agents in Tumors: Physiological Barriers and Strategies. J. Nat'l. Cancer Inst., 81: 570–576, 1989.

What is claimed is:

1. A method for reducing interstitial fluid pressure of tissue comprising:
   implanting in tissue at least a portion of an aspiration probe having an open proximal end coupling the aspiration probe to a suction source to generate suction in the aspiration probe and thereby to reduce interstitial fluid pressure of tissue; and
   inserting a cleaning obturator into the open proximal end of the aspiration probe to debris;
   wherein the at least a portion of the aspiration probe remains implanted in tissue when the aspiration probe is cleaned.

2. method as in claim 1, further comprising inserting a blocking obturator in the aspiration probe when the suction source is not on to prevent debris from accumulating in the aspiration probe.

3. A method as in claim 1, further comprising selectively adjusting the suction source to generate a pressure field to assist in delivery of a pharmacological agent to tissue.

4. A method as in claim 1, further comprising removably connecting to an aspiration probe a connection member having a first end configured and dimensioned for removably connecting with the proximal end of the aspiration probe and a second end configured and dimensioned for removably connecting with the suction source.

5. A method as in claim 1, wherein a suture ring is provided at the proximal end of the aspiration probe, said method further comprising securing the aspiration probe to tissue via the suture ring.

6. A method as in claim 5, wherein a hole is defined in the suture ring, said method further comprising passing suture through said hole to secure the aspiration probe to the tissue via the suture ring.

7. A method as in claim 1, further comprising sliding a cleaning obturator having at least one fin into a chamber in the aspiration probe through the proximal end of the aspiration probe and engaging the fin with at least one slit in the aspiration probe upon insertion of the cleaning obturator into the chamber to remove any debris from the at least one slit.

8. A method as in claim 1, further comprising fitting a blocking obturator within a chamber in the aspiration probe to block at least one slit in the aspiration probe thereby blocking fluid communication between the chamber of the aspiration probe and tissue for preventing accumulation of tissue in the chamber.

9. A method as in claim 8, wherein the blocking obturator includes at least one rib configured and dimensioned to block the at least on slit, said method further comprising inserting at least one rib in the at least one slit to block the at least one slit.

10. A method as in claim 8, further comprising impregnating the blocking obturator with a therapeutically effective amount of a pharmacological agent before fitting the blocking obturator into the chamber of the aspiration probe.

11. A method as in claim 8, wherein providing a blocking obturator further comprises providing a blocking obturator made of a biocompatible polymer.

12. A method as in claim 11, further comprising impregnating the blocking obturator with an antibiotic.

13. A method as in claim 1, wherein:
   a plurality of apertures are defined along the body of the aspiration probe providing fluid communication between a chamber defined in the aspiration probe and the tissue upon insertion of at least a portion of the aspiration probe in the tissue; and
   the cleaning obturator has at least one protrusion;
   said method further comprising engaging the at least one protrusion of the cleaning obturator with the plurality of apertures upon insertion of the cleaning obturator into the chamber of the aspiration probe for removing any debris from the plurality of apertures.

14. A method as in claim 1, further comprising removing the cleaning obturator from the aspiration probe.

15. A method for reducing interstitial fluid pressure of tissue comprising:
   implanting at least a portion of at least two aspiration probes in tissue;
   coupling at least one of the aspiration probes to a suction source to generate suction and thereby to reduce interstitial fluid pressure of tissue;
   delivering a drug to the tissue; and
   assisting delivery of the drug by applying electroporation.

16. A method as in claim 15, wherein suction and electroporation occur simultaneously.

17. A method as in claim 15, further comprising a conducting obturator configured and dimensioned for sliding movement into a chamber and in at least one of the aspiration probes made of an electrically conductive material, said method further comprising using said conducting obturator as an electrode for the electroporation.

18. A method as in claim 15, further comprising:
   fitting a blocking obturator having at least a portion made of an electrically conductive material within a chamber in at least one of the aspiration probes; and
   using the electrically conductive material as an electrode for electroporation.

19. A method as in claim 15, further comprising:
   removably connecting a first end of a connection member with the proximal end of a respective aspiration probe;

removably connecting a second end of the connection member with the suction source;

removably connecting a suction source port of a manifold with the suction source; and removably connecting an aspiration probe port of the manifold with a respective connection member.

20. A method as in claim 19, wherein a chamber is defined in the manifold in fluid communication with each of the aspiration probe ports, said method further comprising collecting aspiration fluid in the chamber.

21. A method as in claim 19, wherein a valve is operatively associated with each of the aspiration probe ports of the manifold, said method further comprising selectively coupling and uncoupling the aspiration probe ports to the suction source.

22. A method as in claim 19, wherein a plurality of chambers are defined in the manifold, said method further comprising fluidly communicating each chamber with one of the aspiration probe ports and collecting aspirated fluid therein.

23. A method as in claim 19, wherein a valve is operatively associated with a suction source port, said method further comprising selectively coupling and uncoupling the valve to the suction source, wherein the valve allows retention of pressure generated by the suction source upon uncoupling from the suction source.

24. A method as in claim 19, further comprising implanting at least a portion of the manifold.

25. A method as in claim 19, further comprising sliding a cleaning obturator into the chamber through the proximal end of one of the aspiration probes and engaging at least one fin on the cleaning obturator with at least one slit in the aspiration probe upon insertion of the cleaning obturator into the chamber to remove any debris from the slit.

26. A method as in claim 19, further comprising implanting at least one drug delivery probe having a body with a proximal end and a closed distal end, an interior chamber defined by the body and proximal and distal ends, and at least one slit along the body providing fluid communication between the chamber of the drug delivery probe and tissue upon insertion of at least a portion of the drug delivery probe in tissue.

27. A method as in claim 19, wherein at least a portion of at least one of the aspiration probes is made of an electrically conductive material, further comprising using the electrically conductive portion of the aspiration probe as an electrode for the electroporation.

28. A method as in claim 19, further comprising separately adjusting the pressure of each of the aspiration probes.

* * * * *

UNITED STATES PATENT AND TRADEMARK OFFICE
CERTIFICATE OF CORRECTION

PATENT NO. : 6,547,777 B2
DATED : April 15, 2003
INVENTOR(S) : Gene R. Diresta and John H. Healey It is certified that error appears in the above-identified patent and that said Letters Patent is hereby corrected as shown below:

Column 1,
Line 10, insert the following paragraph, -- The research disclosed herein was funded in part with United States Government support under NCI Grant No. 08748 and NIH Grant No. CA78494-01A1 from the United States Department of Health and Human Services. The United States Government may have certain rights in this invention. --

Signed and Sealed this

Twenty-ninth Day of June, 2004

JON W. DUDAS
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,547,777 B2 | Page 1 of 1 |
| APPLICATION NO. | : 09/784132 | |
| DATED | : April 15, 2003 | |
| INVENTOR(S) | : Gene R. Diresta and John H. Healey | |

It is certified that error appears in the above-identified patent and that said Letters Patent is hereby corrected as shown below:

Replace the paragraph that starts on column 1, line 10 with -- The research disclosed herein was funded in part with United States Government Support under NCI Grant No. 08748 and NIH Grant No. CA78494-01A1 from the United States Department of Health and Human Services. The United States Government has certain rights in this invention. --

Signed and Sealed this

Twenty-first Day of April, 2009

JOHN DOLL
*Acting Director of the United States Patent and Trademark Office*